United States Patent [19]

Döring et al.

[11] Patent Number: 5,672,791
[45] Date of Patent: Sep. 30, 1997

[54] PROCESS FOR THE PREPARATION OF NUCLEAR-HALOGENATED BENZOTRICHLORIDES FROM THE CORRESPONDING BENZOTRIFLUORIDES

[75] Inventors: Fritz Döring, Odenthal; Reinhold Gehring, Wuppertal; Josef Heinrich, Solingen, all of Germany

[73] Assignee: Bayer Aktiengesellschaft, Leverkusen, Germany

[21] Appl. No.: 590,860

[22] Filed: Jan. 24, 1996

[30] Foreign Application Priority Data

Jan. 31, 1995 [DE] Germany .......... 195 02 942.9

[51] Int. Cl.⁶ ............................... C07C 17/00
[52] U.S. Cl. ............................ 570/191; 570/196
[58] Field of Search ..................... 570/191, 196

[56] References Cited

U.S. PATENT DOCUMENTS

| 1,973,069 | 9/1934 | Henne . | |
|---|---|---|---|
| 3,950,445 | 4/1976 | Ryf | 260/651 |

FOREIGN PATENT DOCUMENTS

| 2546533 | 4/1977 | Germany . |
|---|---|---|
| 4301247 | 7/1994 | Germany . |

*Primary Examiner*—Samuel Barts
*Attorney, Agent, or Firm*—Sprung Horn Kramer & Woods

[57] ABSTRACT

Nuclear-halogenated benzotrichlorides are prepared in a particularly advantageous manner from the corresponding nuclear-halogenated benzotrifluorides by reacting nuclear-halogenated benzotrifluorides with silicon tetrachloride in the presence of catalytic amounts of aluminium trichloride.

11 Claims, No Drawings

PROCESS FOR THE PREPARATION OF NUCLEAR-HALOGENATED BENZOTRICHLORIDES FROM THE CORRESPONDING BENZOTRIFLUORIDES

The present invention relates to a particularly advantageous process for the preparation of nuclear-halogenated benzotrichlorides from the corresponding benzotrifluorides.

It is known from DE-A 43 01 247 that certain nuclear-halogenated benzotrifluorides can be reacted with chlorides from the series of Friedel-Crafts catalysts and the corresponding nuclear-halogenated benzotrichlorides can thus be obtained. Aluminium trichloride, titanium tetrachloride, antimony pentachloride and boron trichloride are mentioned as suitable chlorides. These are employed in amounts of 1 to 1.5 mol per mole of benzotrifluoride. A disadvantage of this process is the necessary handling of chlorinated solvents and the associated low space/time yield. Furthermore, the chlorides from the series of Friedel-Crafts catalysts must be employed in excess, which leads to residues which are difficult to dispose of.

A process has now been found for the preparation of nuclear-halogenated benzotrichlorides from the corresponding nuclear-halogenated benzotrifluorides, which is characterized in that nuclear-halogenated benzotrifluorides are reacted with silicon tetrachloride in the presence of catalytic amounts of aluminium trichloride.

Chlorinated and/or fluorinated benzotrifluorides are suitable, for example, for use in the process according to the invention. 2,3,4,5-Tetrafluoro-, 2,3,5,6-tetrafluoro-, 3-chloro-2,4,5-trifluoro- or 4-chloro-benzotrifluoride are preferably employed, particularly preferably 2,3,4,5-tetrafluorobenzotrifluoride. The nuclear-halogenated benzotrifluorides to be employed are known compounds or are accessible analogously to known compounds.

Silicon tetrachloride can be employed in commercially available quality. 0.7 to 1.5 mol of silicon tetrachloride, for example, can be employed per mole of nuclear-halogenated benzotrifluoride employed. This amount is preferably 0.75 to 1.0 mol, particularly preferably 0.75 mol. Larger excesses of silicon tetrachloride are in general not a disadvantage in principle, but are of no interest from economic considerations.

Aluminium trichloride can be employed, for example, in amounts of 0.01 to 0.2 mol per mole of nuclear-halogenated benzotrifluoride employed. This amount is preferably 0.05 to 0.15 mol.

The process according to the invention can be carried out, for example, at temperatures in the range from 0° to 80° C. Temperatures in the range from 15° to 60° C. are preferred. If nuclear-halogenated benzotrifluorides containing halogen atoms in the p-position are employed, temperatures in the range from 15° to 40° C. are preferred.

The pressure which prevails while carrying out the process according to the invention is not critical. The process can be carded out under normal pressure, reduced pressure or increased pressure. It is preferably carried out under normal pressure.

During the progress of the reaction according to the invention, silicon tetrafluoride is discharged from the reaction mixture. This can be processed in various ways. For example, it can be passed into aqueous sodium hydroxide solution, but it is then in general no longer useable for further use. It can also be absorbed in hydrogen fluoride, hexafluorosilicic acid being obtained, which can be used, for example in a manner known per se, for example as a preservative or cleaning agent. Silicon tetrafluoride can furthermore also be collected in an alcohol, and the silicon tetrafluoride can be recovered from this and used in a manner known per se, for example for the preparation of highly disperse silicon dioxide or for increasing the stability of concrete (Ocart process).

The reaction according to the invention can be carried out in apparatuses made of customary materials. Suitable materials for carrying out the reaction on an industrial scale are, for example, high-grade steels.

After the process according to the invention has been carried out, a reaction mixture is in general present which, in addition to the desired reaction product, comprises a mass, which comprises aluminium salts, and if appropriate excess silicon tetrachloride. Excess silicon tetrachloride can be separated off, for example, by distillation and employed again in a further batch. The mass comprising aluminium salts can be separated off from the nuclear-halogenated benzotrichloride prepared, for example by filtration. The mass comprising aluminium salts which has been separated off can be employed again in a further batch instead of fresh aluminium trichloride. If the mass comprising aluminium salts is recycled repeatedly, it is advantageous to add fresh aluminium trichloride from time to time, for example 10 to 25% by weight of the amount of aluminium trichloride originally employed, for example after every 2nd to 5th recycling step.

The filtrate from the removal of the mass comprising aluminium salts often consists of highly pure halogenated benzotrichloride which can be further used directly. If desired, the nuclear-halogenated benzotrichloride can be further purified, for example by distillation, preferably under reduced pressure.

Nuclear-halogenated benzotrichlorides are important intermediate products for the preparation of quinolonecarboxylic acid derivatives, which are antibacterial active compounds (see, for example, DE-A 3 420 796 and EP-A 417 669).

In addition to high yields in the region of 90% or more, the process according to the invention has a number of further advantages. Thus, only catalytic amounts of aluminium trichloride are used. Due to the possibility of recycling, only very small amounts of waste products to be disposed of are formed. The space/time yields are high, since the process is carried out without a solvent. Working up of the reaction mixtures is very simple, since the by-product silicon tetrafluoride escapes from the reaction mixture in gaseous form.

EXAMPLES

Example 1

Preparation of 4-chlorobenzotrichloride 13.5 g of aluminium trichloride (anhydrous) and 180.5 g of 4-chlorobenzotrifluoride were initially introduced into a 1 l stirred flask provided with a dropping funnel and reflux condenser and the mixture was heated to 50° C. 170 g of silicon tetrachloride were added dropwise in the course of 2 hours, while stirring. The silicon tetrafluoride waste gas obtained during the reaction was passed on to dilute aqueous sodium hydroxide solution in a stirred polyethylene pot, while being admixed with nitrogen. Dilute aqueous sodium hydroxide solution (about 2.5% strength) was constantly subsequently metered in by means of a pump in accordance with the amount of waste gas passed in, and a discharge was removed continuously by a siphon at the base of the vessel. When the addition of the silicon tetrachloride had ended, the reaction mixture was subsequently stirred for 3 hours and then distilled in vacuo until dry aluminium salt was present.

Result:

1st Fraction, pressure 1,013 to 1,015 mbar, 31 g of silicon tetrachloride

2nd Fraction, boiling point 112° to 115° C./15 mbar, 208 g of 4-fluorobenzotrichloride (content according to GC 99%, $n_D^{20}$=1.5712, yield: 89.5% of theory)

Example 2

Preparation of 2,3,4,5-tetrafluorobenzotrichloride

The procedure was as described in Example 1. 20 g of aluminium trichloride (anhydrous) and 218 g of 2,3,4,5-tetrafluorobenzotrifluoride (96% pure) were initially introduced into the reaction vessel. 170 g of silicon tetrachloride were then added dropwise at 50° C. in the course of 2 hours, while stirring. Distillation gave:

1st Fraction, pressure 1,013 to 20 mbar, 35 g of silicon tetrachloride

2nd Fraction, boiling point 50° to 55° C./4 mbar, 238 g of 2,3,4,5-tetrafluorobenzotrichloride Yield: 88.9% of theory)

Example 3

Preparation of 2,4,5-trifluoro-3-chlorobenzotrichloride

The procedure was as described in Example 1. 234.5 g of 2,4,5-trifluoro-3-chlorobenzotrifluoride (98% pure) and 13.5 g of aluminium trichloride (anhydrous) were initially introduced into the reaction vessel. 70 g of silicon tetrachloride were then added dropwise at 50° to 55° C. in the course of 1.5 hours, and the mixture was subsequently stirred at this temperature for a further 4 hours.

Distillation gave:

1st Fraction, pressure 1,013 to 20 mbar, 30 g of silicon tetrachloride

2nd Fraction, boiling point 72° to 76° C./2 mbar, 274 g of 2,4,5-trifluoro-3-chlorobenzotrichloride (content according to GC 97%, yield: 95.5% of theory)

What is claimed is:

1. A process for the preparation of a nuclear-halogenated benzotrichloride from the corresponding nuclear-halogenated benzotrifluoride, in which the nuclear-halogenated benzotrifluoride is reacted with silicon tetrachloride in the presence of a catalytic amount of aluminium trichloride.

2. The process of claim 1, in which 2,3,4,5-tetrafluoro-, 2,3,5,6-tetrafluoro-, 3-chloro-2,4,5-trifluoro- or 4-chlorobenzotrifluoride is employed.

3. The process of claim 1, in which 0.7 to 1.5 mol of silicon tetrachloride are employed per mole of benzotrifluoride employed.

4. The process of claim 1, in which 0.01 to 0.2 mol of aluminium trichloride is employed per mole of halogenated benzotrifluoride employed.

5. The process of claim 1, which is carried out at temperatures in the range from 0° to 80° C.

6. The process of claim 1, which, if halogenated benzotrifluorides containing halogen atoms in the p-position are employed, is carried out at temperatures in the range from 15° to 40° C.

7. The process of claim 1, in which the silicon tetrafluoride discharged from the reaction mixture during the reaction is passed into aqueous sodium hydroxide solution.

8. The process of claim 1, in which the silicon tetrafluoride discharged from the reaction mixture during the reaction is absorbed in hydrogen fluoride.

9. The process of claim 1, in which the silicon tetrafluoride discharged from the reaction mixture during the reaction is collected in an alcohol.

10. The process of claim 1, in which for working up the reaction mixture, any excess silicon tetrachloride present is first separated off by distillation and a mass comprising aluminium salts is separated off by filtration from the nuclear-halogenated benzotrichloride prepared.

11. The process of claim 10, in which in the reaction according to the invention, the mass comprising aluminium salts which has been separated off from the reaction mixture of a preceding batch is employed instead of fresh aluminium trichloride.

* * * * *